United States Patent
Bjorkholm

(10) Patent No.: US 6,272,206 B1
(45) Date of Patent: Aug. 7, 2001

(54) ROTATABLE CYLINDER DUAL BEAM MODULATOR

(75) Inventor: Paul J. Bjorkholm, Newport Beach, CA (US)

(73) Assignee: PerkinElmer Detection Systems, Inc., Cypress, CA (US)

( * ) Notice: Subject to any disclaimer, the term of this patent is extended or adjusted under 35 U.S.C. 154(b) by 0 days.

(21) Appl. No.: 09/433,276

(22) Filed: Nov. 3, 1999

(51) Int. Cl.[7] .......................... G01N 23/00; G01N 23/201
(52) U.S. Cl. ............................ 378/146; 378/149; 378/150
(58) Field of Search .................................. 378/146, 147, 378/148, 149, 150

(56) References Cited

U.S. PATENT DOCUMENTS

| 3,808,444 | 4/1974 | Schneeberger et al. | 378/57 |
|---|---|---|---|
| 4,745,631 | 5/1988 | Paolini | 378/146 |
| 4,769,829 * | 9/1988 | Webb et al. | 378/146 |
| 4,995,066 * | 2/1991 | Harding et al. | 378/146 |
| 5,181,234 | 1/1993 | Smith | 378/146 |
| 5,282,656 | 2/1994 | Fizer . | |
| 5,493,546 | 2/1996 | Kasahara . | |
| 5,493,596 | 2/1996 | Annis | 378/146 |

* cited by examiner

Primary Examiner—Drew Dunn
(74) Attorney, Agent, or Firm—Iandiorio & Teska

(57) ABSTRACT

A dual beam modulator (10) includes a rotatable cylinder (12) having annular walls (14, 15) and a set of a plurality of discrete chordal passages (18) extending through the walls between opposing holes in the outer surface of cylinder walls (14, 15). Each of the passages (18) is spaced radially about each of the walls (14, 15) and longitudinally in the direction of the longitudinal axis of the cylinder (12) for producing, in response to an incident fan beam of radiation (30), a series of discrete pencil beams (28) as the cylinder (12) rotates. The cylinder (12) further has reduced radius sections (16, 17) on the outer surface of the walls (14, 15) for periodically passing the incident fan beam (30) alternately with the series of pencil beams (28) as the cylinder (12) rotates.

9 Claims, 2 Drawing Sheets

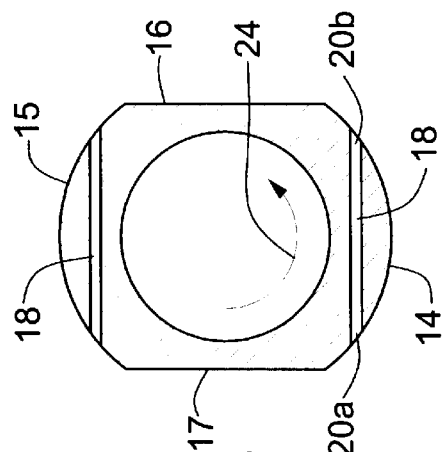
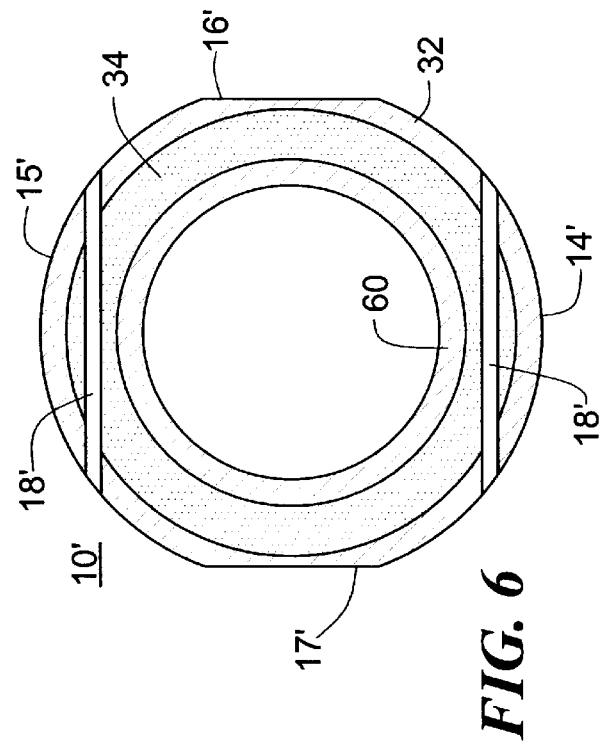
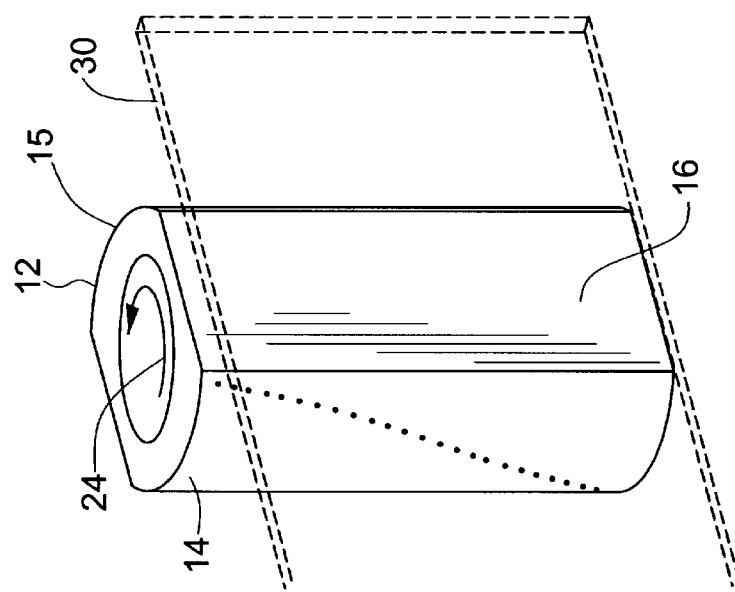

ROTATABLE CYLINDER DUAL BEAM MODULATOR

FIELD OF INVENTION

This invention relates to a dual beam modulator capable of providing both a series of discrete pencil beams and a fan beam particularly useful in X-ray imaging devices.

BACKGROUND OF INVENTION

X-ray beam collimators form an unshaped X-ray beam into a specific, desired shape. Fan beam collimators simply use a lead sheet or other blocking material with a slit in it to form a fan beam. See U.S. Pat. No. 3,808,444. Chopper wheel collimators use a plurality of generally radial slots to chop a fan beam into pencil beams. See the above patent and U.S. Pat. No. 5,181,234. These are often called flying spot scanners because the pencil beam moves cross-wise back and forth or up and down as the chopper wheel rotates. See also U.S. Pat. No. 4,745,631. A rotating wheel collimator has an X-ray source at its center and a plurality of radial channels extending outward to create pencil beams. See U.S. Pat. No. 5,493,546. Two other designs use helical slits to create a continuous or flying spot pencil beam from a fan beam. In one approach, U.S. Pat. No. 4,745,631, there are helical slits on the surface of a cylinder which create a fly spot pencil beam as the cylinder rotates. In another approach there is a helical slit on the surface of the cylinder. See U.S. Pat. Nos. 5,493,596 and 5,528,656.

BRIEF SUMMARY OF THE INVENTION

It is therefore an object of this invention to provide an improved dual beam modulator.

It is a further object of this invention to provide such an improved dual beam modulator which produces both pencil and fan beams.

It is a further object of this invention to provide such an improved dual beam modulator which leaves the center of the modulator free for simple drive mechanisms and reinforcing structure.

It is a further object of this invention to provide such an improved dual beam modulator which provides a series of discrete pencil beams.

It is a further object of this invention to provide such an improved dual beam modulator which is simple in design and can be made smaller and more compact.

It is a further object of this invention to provide such an improved dual beam modulator which is easier and less expensive to manufacture.

The invention results from the realization that a simpler, smaller, more compact beam modulator which forms both pencil and fan beams and which can be easily rotated with a central drive can be achieved by locating a plurality of discrete chordal passages through the annular wall of a rotatable cylinder with each passage being spaced radially and longitudinally in a series about the wall and providing reduced radius sections on opposite sides of the cylinder so that rotation of the cylinder alternately passes an incident fan beam or modulates it into a series of discrete pencil beams.

This invention features a dual beam modulator includes a rotatable cylinder having an annular wall. There is a plurality of discrete chordal passages extending through the wall between opposing holes on its outer surface. Each of the passages is spaced radially about the wall and longitudinally in the direction of the longitudinal axis of the cylinder for producing in response to an incident fan beam of radiation a series of discrete pencil beams as the cylinder rotates. The cylinder has a reduced radius section on the outer surface of the wall for periodically passing the incident fan beam alternately with the series of pencil beams as the cylinder rotates.

In a preferred embodiment the cylinder may be a circular cylinder or it may be a polygonal cylinder. The reduced radius section may be flat and it may be a chordal planar surface. The passages may be approximately 1–10 mm diameter and may be spaced radially approximately 1°–5° and longitudinally approximately $1/10$–$1/500$ of the angular range. The reduced radius section may subtend an angle of approximately 10°–180°. The cylinder may be made of lead loaded epoxy. The annular wall may form an internal chamber for receiving a drive shaft. The chamber may be centrally disposed coincident with the longitudinal axis of the cylinder. There may be a drive mechanism for rotating the cylinder. The drive mechanism may rotate the cylinder at approximately 100–2000 rpm. The cylinder may have an outer diameter of 5–30 inches. There may be a number of reduced radius sections and a number of sets of a plurality of discrete chordal passages.

BRIEF DESCRIPTION OF THE DRAWINGS

Other objects, features and advantages will occur to those skilled in the art from the following description of a preferred embodiment and the accompanying drawings, in which:

FIGS. 1–4 are three-dimensional diagrammatic views of a dual beam modulator according to this invention; and FIG. 5 is a top cross-sectional view of the cylinder shown in FIG. 1 taken along line 5—5; and FIG. 6 is a top cross-sectional view of a specific embodiment of a dual beam modulator according to this invention.

DISCLOSURE OF PREFERRED EMBODIMENT

Figure 3:
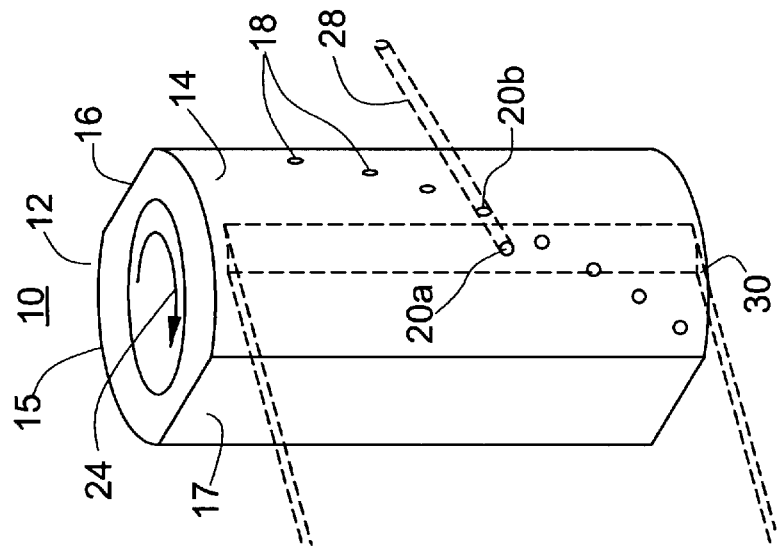
Figure 2:
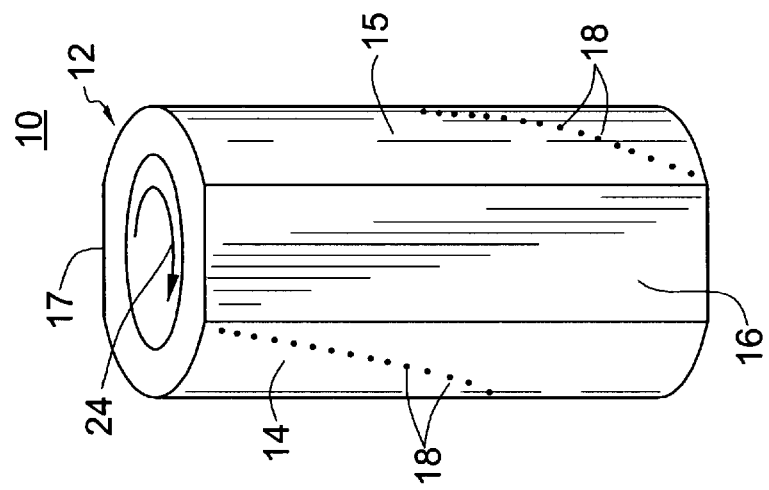
Figure 1:
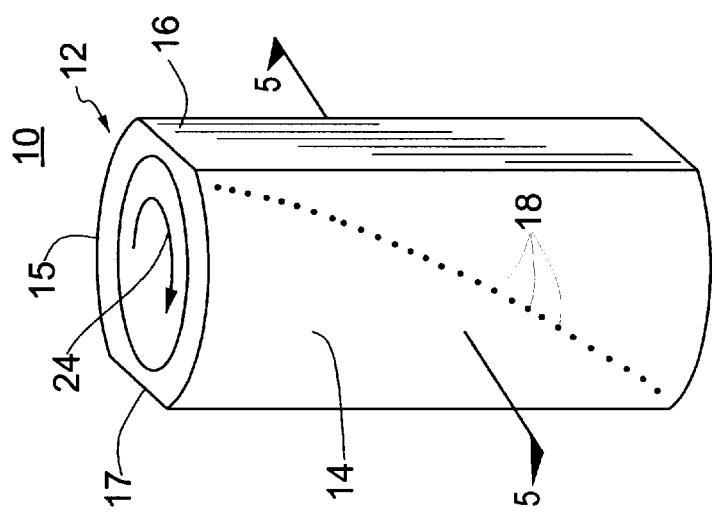

In this invention, a dual beam modulator rotates first producing a series of discrete pencil beams of X-rays which impinge, for example, on a backscatter detector after scattering off a target to be imaged with X-rays. The modulator then rotates further producing a fan beam of X-rays which strikes a transmission detector after passing through the target. The modulator then again produces pencil beams as it rotates and a fan beam such that each full revolution of the modulator produces: a first series of many pencil beams which strike the target from its bottom to its top one after the other, a first fan beam which strikes the target and extends from the bottom to the top of the target, a second series of many pencil beams, and a second fan beam.

There is shown in FIGS. 1–4 a dual beam modulator 10 according to this invention including a cylinder 12 which has annular walls 14 and 15 and reduced radius sections 16 and 17 therebetween. There are a plurality of discrete chordal passages or tunnels 18 which extend through annular wall 14 between entrance holes and exit holes on the outside of wall 14. The same is true with respect to annular wall 15, FIG. 2: there are a plurality of discrete chordal passages or tunnels 18 which extend through annular wall 15 between entrance holes and exit holes in the outside of wall 15. A fan beam of X-rays 30, FIG. 3, strikes cylinder 14 and as cylinder 12 rotates in the direction of arrow 24, a plurality of individual discrete pencil beams 28 are created. At the particular moment shown in FIG. 3, the passage 18 through annular wall 14 associated with entrance hole 20a and exit hole 20b creates pencil beam 28 by passing a discrete portion of the incident fan beam 30. See also FIG. 5. As entrance hole 20a rotates beyond the area where fan beam 30 strikes annular surface 14, exit and entrance holes 20a and 20b provide a distinct and sharp cut off of pencil beam 28 which thus results in distinct and more exact on and off times for the series of pencil beams produced by passages or tunnels 18. The source of the fan beam is not shown, as any suitable source such as disclosed in the references cited in the Background of the Invention above may be used. The references cited in the Background of the Invention are incorporated herein in their entirety by this reference.

As cylinder 12 rotates, one after another of the passages 18, FIG. 5 come into alignment with incident fan beam 30, FIG. 3 to produce a series of discrete pencil beams 28. As cylinder 12 continues to rotate in the direction of arrow 24, it reaches the position as shown in FIG. 4, where the reduced radius section 16 permits fan beam 30 to pass unmodulated. Although reduced radius section 16 is shown as a planar or chordal surface, this is not a necessary limitation of the invention as any suitable reduced radius form or shape that passes fan beam 30 will suffice.

The passages 18 that run from the entrance holes to the exit holes in surfaces 14 and 15 are preferably stepped or angled in two directions, that is, both radially and longitudinally, about cylinder 12 in annular walls 14 and 15. Although thus far the cylinder 12 is shown as a right circular cylinder this is not a necessary limitation of the invention as it may take any shape (e.g., a polygon) from which the desired beams can be formed.

Cylinder 12 may be made of any suitable X-ray blocking material such as lead loaded epoxy. The chordal passages 18 extending through annular surfaces 14 and 15 may have a diameter typically of 1–10 mm and may be spaced apart radially by an amount of 1–5 degrees and longitudinally by an amount $1/10$ to $1/500$ of the total angular range while the reduced radius section may subtend an angle of approximately 10–180° with a cylinder having a diameter of 5–30 inches, a height sufficient to cover the fan beam, and rotated typically by a motor at the rate of 100–2000 rpm.

The result is a dual (pencil and fan) beam modulator in which the X-ray beams do not pass through the center of the modulator which thus can be easily reinforced and incorporated with drive motors and drive shafts. Two reduced radius sections 17 and 16 are shown in the preferred embodiment for balance but only one reduced radius section may be used in other embodiments. The pencil beams produced by the modulator are useful for forming backscatter images while the fan beams produced by the modulator are useful for forming transmission images.

In one specific embodiment, modulator 10' includes inner pipe 60 and outer pipe 32 with lead filling 34 therebetween. Chordal passages 18 extend through annular surfaces 14' and 15' of outer pipe 32 and also, in some cases, through lead filling 34. Reduced radius sections 16' and 17' are formed by machining outer pipe 32.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. A dual beam modulator comprising:

a rotatable cylinder including at least one annular wall;

a set of a plurality of discrete chordal passages extending through said wall between opposing holes on its outer surface, each of said passages being spaced radially about said wall and longitudinally in the direction of the longitudinal axis of said cylinder for producing in response to an incident fan beam of radiation a series of discrete pencil beams as the cylinder rotates;

at least one reduced radius section on the cylinder for periodically passing the incident fan beam unmodulated alternately with the series of pencil beams as the cylinder rotates.

2. The dual beam modulator of claim 1 in which said cylinder is a circular cylinder.

3. The dual beam modulator of claim 1 in which said reduced radius section is flat.

4. The dual beam modulator of claim 1 in which said passages are approximately 1 to 10 mm in diameter.

5. The dual beam modulator of claim 1 in which said passages are spaced radially approximately 1 to 5 degrees.

6. The dual beam modulator of claim 1 in which said passages are spaced longitudinally approximately $1/10$ to $1/500$ of the total angular range.

7. The dual beam modulator of claim 1 in which said reduced radius section subtends an angle of approximately 10 to 180 degrees.

8. The dual beam modulator of claim 1 in which the cylinder is made of lead loaded epoxy.

9. The dual beam modulator of claim 1 in which the rotatable cylinder includes an inner pipe and an outer pipe with a lead filling therebetween, the reduced radius section machined in the outer pipe, the discrete chordal passages extending through the outer pipe.

\* \* \* \* \*